United States Patent [19]

Ruth

[11] 4,170,548
[45] Oct. 9, 1979

[54] ENERGY EFFICIENT DISTILLATION PROCESS

[75] Inventor: Ralph G. Ruth, Tulsa, Okla.

[73] Assignee: Dresser Engineering Company, Tulsa, Okla.

[21] Appl. No.: 848,612

[22] Filed: Nov. 4, 1977

[51] Int. Cl.$^2$ .......................... B01D 3/14; C10G 7/00
[52] U.S. Cl. ...................................... 208/351; 203/81; 203/82; 208/354; 208/355
[58] Field of Search ....................... 208/351, 354, 355; 203/81, 82

[56] References Cited

U.S. PATENT DOCUMENTS

| | | | |
|---|---|---|---|
| 2,666,019 | 1/1954 | Winn et al. | 208/351 |
| 3,368,966 | 2/1968 | Borst et al. | 208/351 |

*Primary Examiner*—Herbert Levine
*Attorney, Agent, or Firm*—James H. Chafin

[57] ABSTRACT

An energy efficient process for the separation of two close boiling point components contained in a multicomponent feed stream. The feed stream is distilled in a first column to produce a relatively light fraction containing substantially all the more volatile close boiling point component, along with part of the less volatile close boiling point component and a bottoms product. The relatively light overhead fraction from the first column is fed to a second column to produce an overhead product, consisting substantially of the more volatile close boiling point component and a bottoms product consisting substantially of the less volatile boiling point component. The bottoms product from the first column is fed to a third column to produce an overhead vapor consisting substantially of the less volatile close boiling point component, which overhead vapor is passed to the second column to supply part of the reboiling energy requirements for said column. A portion of the bottoms product from the second column is recycled to the top of the third column for use as reflux.

3 Claims, 1 Drawing Figure

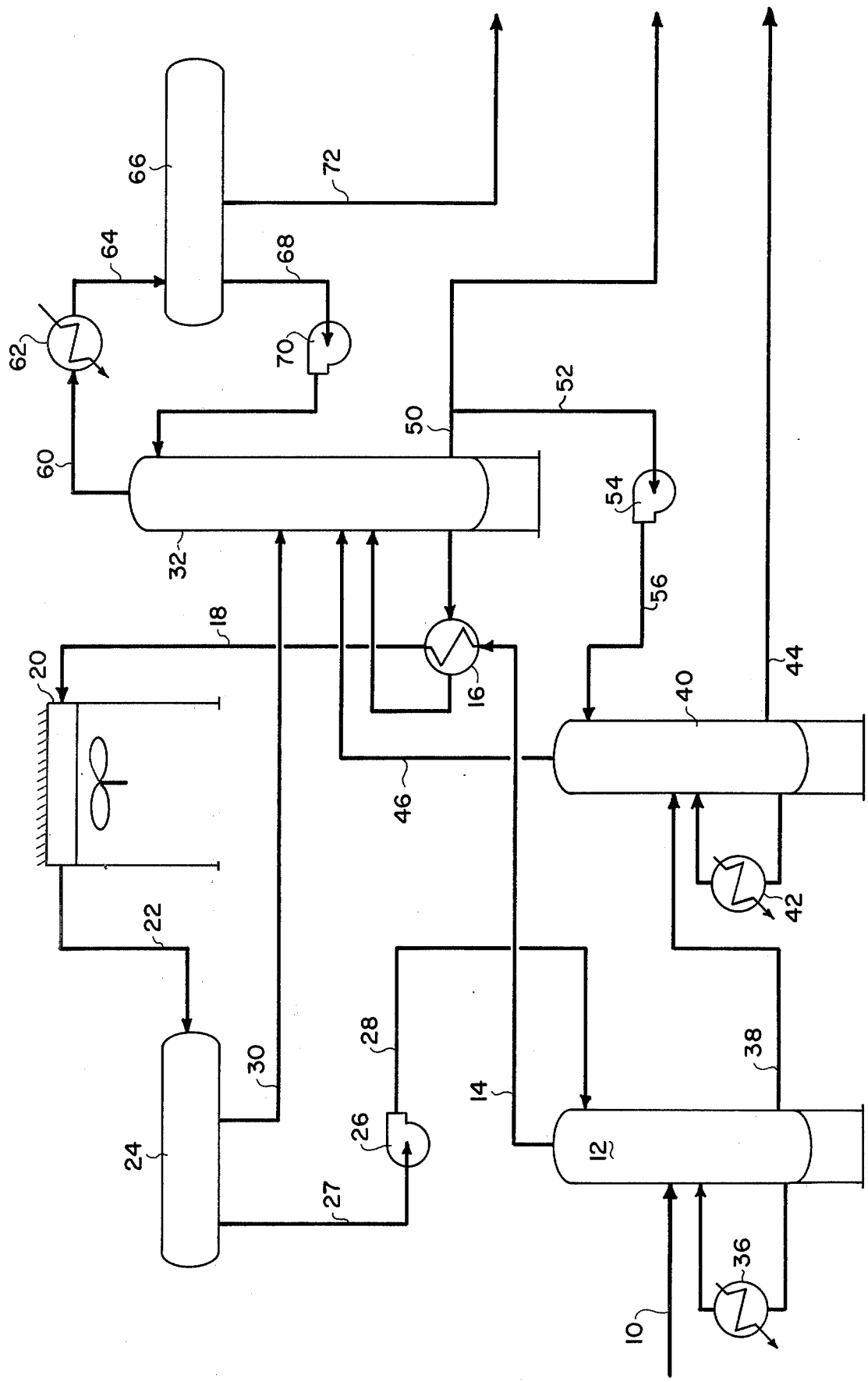

ENERGY EFFICIENT DISTILLATION PROCESS

BACKGROUND OF THE INVENTION

1. Field of the Invention

This invention generally relates to an energy efficient fractionation method for the separation of two close boiling point components from a multi-component mixture. The process is particularly applicable to the separation of isobutane and normal butane from a depropanized gasoline feed stream, resulting in energy savings of approximately 50% over conventional methods.

2. Description of the Prior Art

Many refinery and petrochemical processes require relatively pure quantities of various isomers of a single homologous hydrocarbon series as raw materials. These substances are commonly found mixed with a myriad of other substances in natural gas and crude oil sources. Problems arise however in industrial separation of the isomers due to the closeness in isomer boiling points. This closeness in boiling points and volatility usually requires a large number of equilibrium contacting stages in the fractionating equipment in addition to the use of high reflux ratios to effect the desired separation and product quality. The higher the reflux ratio required, the more energy is necessary for reboiling and condensing the internal tower streams. This increased energy has as a necessary correlary, larger auxiliary equipment to facilitate the greater energy transfer.

It is therefore an object of this invention to provide an energy efficient fractionation process for the separation of two close boiling point components in a multi-component system, which may be easily and economically incorporated into existing designs.

SUMMARY OF THE INVENTION

In accordance with the invention, a fluid separation process is disclosed for the separation of two close boiling point components such as homologous isomers contained in a multi-component feed stream. The process disclosed can result in energy savings of as much as 50% over conventional systems.

A multi-component feed stream, such as depropanized gasoline containing normal and isobutane is distilled in a first column to produce a relatively light overhead fraction containing substantially all of the more volatile close boiling point component along with part of the less volatile close boiling point component and a bottoms product. The relatively light overhead fraction frome of the first column is fed to a second column to produce an overhead product consisting substantially of the more volatile close boiling point component and a bottoms product consisting substantially of the less volatile boiling point component. The bottoms product from the first column is fed to a third column to produce an overhead vapor consisting substantially of the less volatile close boiling point component, which overhead vapor is injected directly to the bottom of the second column to supply part of the reboiling energy requirements thereof. A portion of the bottoms product from the second column is recycled to the top of the third column for use as reflux.

BRIEF DESCRIPTION OF THE DRAWINGS

The drawing attached hereto illustrates a preferred embodiment of the process for separating normal and isobutanes from a depropanized gasoline feed.

DETAILED DESCRIPTION OF THE PREFERRED EMBODIMENT

The following description of the present invention is limited to a process scheme for separating normal and isobutane from a depropanized gasoline feed stream, as such a process is illustrative of the general principles involved as well as being a practical example of an industrial use of the invention. It should be understood, however, that description of such an embodiment for the particular named components and the equipment arrangement specified is not intended as limiting the invention to same.

Referring now to the drawing which illustrates the process schematically, depropanized gasoline at approximately 200° F. enters feed preparation tower 12 at an intermediate tray location by means of line 10. The depropanized gasoline typically contains less than 1 mol % propane, approximately 65 mol % butane, 25 mol % pentane and the balance, hexane and heavier hydrocarbons, with a ratio of normal to isobutane of 3:1. The feed preparation tower 12 is a fractionator preferably having a sufficient number of equilibrium stages to produce a compostion in the overhead vapor leaving the tower of approximately 35 mol % isobutane and 64 mol % normal butane under moderate reflux conditions. The overhead vapor from tower 12 passes via line 14 to a condenser reboiler 16 where the overhead vapors are condensed to liquid. From the condenser reboiler the condensed overhead liquid passes via line 18 to an air sub cooler 20 for further cooling. The liquid is preferably subcooled about 20° F. then passes from the subcooler through line 22 to reflux accumulation drum 24. Pipe 27 is connected between the reflux accumulator drum 24 and the suction port of pump 26. Line 28 is connected between the discharge port of pump 26 and the top of tower 12. A portion of the subcooled condensed liquid accumulated in drum 24 is returned by pump 26 to the top of the tower for reflux via lines 27 and 28.

The balance of the condensed overhead collected from tower 12 comprised of approximately 35 mol % isobutane and 64 mol % normal butane passes from the reflux accumulator drum via line 30 as feed for splitter column 32.

Reboiling energy for tower 12 is supplied by a conventional reboiler 36 operatively connected to the lower section of the tower. Tower 12 is preferably operated at about 145 psia with a bottom temperature of approximately 230° F. and a top temperature of approximately 165° F.

Line 38 is connected from the bottom of tower 12 to the feed tray of tower 40. The bottoms product from tower 12, comprised of approximately 33 mol % normal butane and heavier hydrocarbons, passes through line 38 to tower 40 for the final separation of the normal butane from the balance of the multi-component stream.

Tower 40 preferably operates at approximately 115 psia with a bottoms temperature of approximately 250° F. Reboil energy is supplied by a conventional reboiler 42 operably connected to the lower section of the tower. Debutanized gasoline containing approximately 1 mol % butane is taken as a bottom product from the tower via line 44 connected thereto. The gasoline leaves the tower at approximately 250° F. and should be used as an indirect heat source prior to storage.

The overhead vapor leaving tower 40, via line 46, consisting substantially of normal butane at 155° F. is injected directly to the bottom section of splitter 32 to provide part of the reboil energy required in said tower. The remaining reboil energy required is supplied by the heat given up through the condensation of the overhead vapor from tower 12 in condenser reboiler 16 which is operatively connected to splitter 32.

A bottoms product stream, comprised approximately of 99 mol % normal butane is withdrawn from the splitter tower 32 via line 50. Line 52 is connected between line 50 and the suction port of pump 54. Line 56 is connected between the discharge port of pump 54 and the top of tower 40. A portion of the bottoms product stream is recycled via line 52, pump 54 and line 56 to the top of tower 40 for reflux as the reflux composition is substantially the same as that of the overhead vapor leaving tower 40.

The overhead vapor from splitter 32 comprised of 98 mol % isobutane, leaves the tower via line 60, is condensed in exchanger 62 and passes from exchanger 62 via line 64 to accumulation drum 66. A portion of the condensed overhead is returned via line 68 and pump 70 to the top of splitter 32 for reflux and the remainder is withdrawn as product from the accumulator via line 72.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A process for separation of two close homologous isomers boiling point components contained in a multi-component hydrocarbon feed stream which comprises:
   distilling the feed stream in a first column, under moderate reflux conditions, to produce a relatively light, totally condensed, fraction containing substantially all of the more volatile close boiling point component along with part of the less volatile close boiling point component and a bottoms product;
   distilling the relatively light fraction from the first column in a second column to produce an overhead product consisting substantially of the more volatile close boiling point component and a bottoms product consisting substantially of the less volatile bottoms product component;
   feeding the bottoms product from the first column to a third column to produce an overhead vapor consisting substantially of the less volatile close boiling point component;
   passing the overhead total vapor from the third column directly to the second column to supply part of the reboiling energy requirement for said second column; and
   recycling a portion of the bottoms product from the second column for use as reflux in the third column.

2. A process as recited in claim 1 wherein part of the reboiling energy requirements for the second column is supplied by the heat released during condensation of the relatively light overhead fraction from the first column.

3. A process as recited in claim 1 wherein the close boiling point components in a multi-component feed stream are butane isomers contained in a depropanized gasoline.

* * * * *